Figure 1:
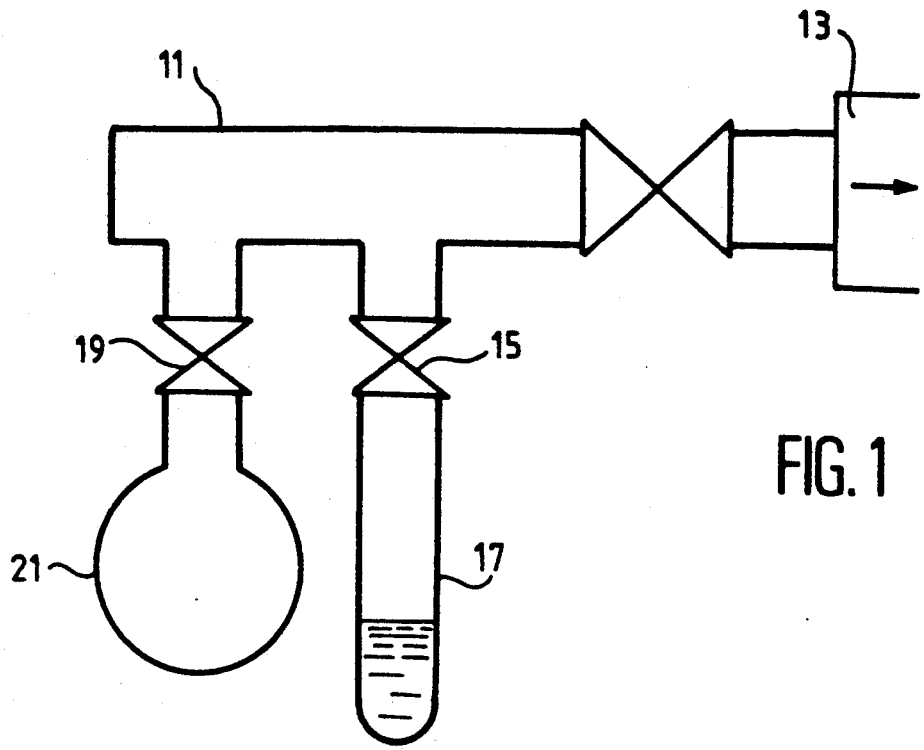

United States Patent [19]

Moussavi

[11] Patent Number: 5,258,313
[45] Date of Patent: * Nov. 2, 1993

[54] PROCESS FOR THE DETECTION OR DETERMINATION OF OXYGEN BY EPR SPECTROMETRY USING RADICAL LITHIUM PHTHALOCYANINES AND COMPOSITION USABLE FOR IN VIVO DETERMINATION

[75] Inventor: Mehdi Moussavi, Saint Egreve, France

[73] Assignee: Commissariat a l'Energie Atomique, Paris, France

[ * ] Notice: The portion of the term of this patent subsequent to Feb. 26, 2008 has been disclaimed.

[21] Appl. No.: 723,188

[22] Filed: Jun. 28, 1991

[30] Foreign Application Priority Data

Jul. 10, 1990 [FR] France .................. 90 08738

[51] Int. Cl.$^5$ .................. G01N 33/00; G01N 24/10
[52] U.S. Cl. .................. 436/136; 436/127; 436/138; 436/173; 514/410; 540/139
[58] Field of Search ............. 436/127, 136, 138, 173; 514/410; 540/139

[56] References Cited

U.S. PATENT DOCUMENTS

| 3,702,831 | 11/1972 | Chiarelli et al. | 436/173 X |
| 4,593,248 | 6/1986 | Hyde et al. | 324/317 |
| 4,996,311 | 2/1991 | Moussavi et al. | 540/139 |
| 5,112,597 | 5/1992 | Moussavi | 514/410 |

FOREIGN PATENT DOCUMENTS 0352182 1/1990 European Pat. Off. .

OTHER PUBLICATIONS

Sugimoto et al. "Stable Free Radicals of Phthalocyanine" *J. Chem. Soc., Chem. Commun.* 1983, 622–623.
H. M. Swartz "The Use of Nitroxides in Viable Biological Systems: an Opertunity and Ehallenge for Chemists and Biochemists" *Pure & Appl. Chem.* 1990, 62, 235–239.
Solid State Communications, vol. 63, No. 8, 1987, pp. 741–744, Ph. Turek et al.: "Extreme spin exchange narrowing in a neutral phthalocyanine radical: The lithium phthalocyanine [1]".
Mol. Cryst. Liq. Cryst. vol. 176, 1989, pp. 535–536, P. Turek et al.: "Septet spin state in the lithium phthalocyanine pi-radical compound. Role of dioxygen".
J. Magn. Reson. vol. 85, No. 1, 1989, pp. 50–59, R. K. Woods et al.: "Spectral-Spatial ESR imaging as a method of noninvasive oximetry".
Europhys. Lett., vol. 8, No. 3, 1989, pp. 275–280, Ph. Turek et al.: "Magnetic properties of the lithium phthalocyanine pi-radical. Role of dioxygen".

*Primary Examiner*—James C. Housel
*Assistant Examiner*—Arlen Soderquist
*Attorney, Agent, or Firm*—Oblon, Spivak, McClelland, Maier & Neustadt

[57] ABSTRACT

The present invention relates to a process for the detection or determination of molecular oxygen by EPR spectrometry using radical lithium phthalocyanines and a composition usable for in vivo determination. In the process, a medium is contacted with a radical lithium phthalocyanine in accordance with the formula:

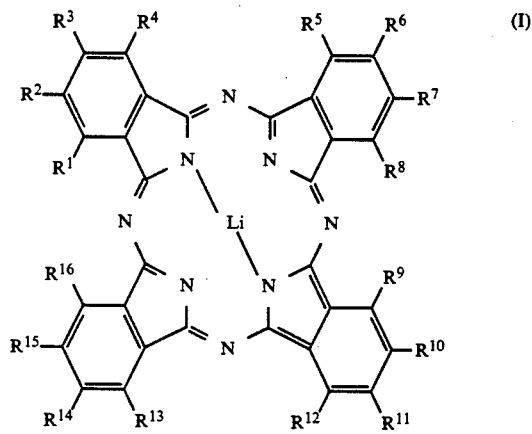

in which $R^2$, $R^3$, $R^6$, $R^7$, $R^{10}$, $R^{11}$, $R^{14}$ and $R^{15}$ represent an alkyl or an alkoxy radical group with 1–3 carbon atoms and $R^1$, $R^4$, $R^5$, $R^8$, $R^9$, $R^{12}$, $R^{13}$ and $R^{16}$ represent a hydrogen or deuterium atom, and the EPR signal of the radical lithium phthalocyanine in contact with the medium is examined.

10 Claims, 3 Drawing Sheets

PROCESS FOR THE DETECTION OR DETERMINATION OF OXYGEN BY EPR SPECTROMETRY USING RADICAL LITHIUM PHTHALOCYANINES AND COMPOSITION USABLE FOR IN VIVO DETERMINATION

The present invention relates to a process for the in vitro or in vivo determination of molecular oxygen in a medium and more particularly usable for the in vivo determination of intra-cellular oxygen.

The determination of molecular oxygen present in certain organs of the human body is an interesting investigation means, because it makes it possible to detect the diseased cells of the organ, which have below normal oxygen contents.

It has recently been found that it was possible to measure the molecular oxygen concentration by electronic para-magnetic resonance (EPR). This procedure uses a radical tracer, whose EPR characteristics, such as the line width, vary significantly as a function of the oxygen content of the medium in which it is located. EPR spectrometry molecular oxygen determination methods are e.g. described in Swartz, Pure & Appl. Chem., vol. 62, no. 2, pp. 235–239, 1990; Woods et al, Journal of Magnetic Resonance, no. 85, pp. 50–59, 1989.

For measuring the intracellular oxygen concentration by this method, a radical substance is injected or implanted in the medium or organ whose oxygen content is to be revealed and then said substance is examined whilst it is in the said medium using an electronic paramagnetic resonance spectrometer. On the basis of the EPR line width obtained, it is possible to deduce the oxygen content of the medium by referring to a prior calibration curve of a sample of the radical substance giveing the relation between the EPR line width and the oxygen content.

The radical substances used in such processes must have different properties. Thus, they must be biocompatible and have EPR characteristics, which in particular change as a function of the oxygen content of the medium at least in the concentration range to be followed, which is 0 to 10% molecular oxygen in the case of human organs which it is of interest to examine.

Among the radical substances usable in such processes, consideration has already been given to the use of 2,2,6,6-tetramethylpyridine-N-oxyl-4-one (TANO), but the latter has the disadvantage of only having a limited variation of its EPR characteristics in the most interesting oxygen concentration range (0 to 10%).

The present invention is directed at a process for the determination or detection of molecular oxygen in a medium, which uses radical substances having a better sensitivity than TANO.

According to the invention, the process for the detection or determination of molecular oxygen in a medium consists of contacting with the said medium a radical lithium phthalocyanine in accordance with the formula:

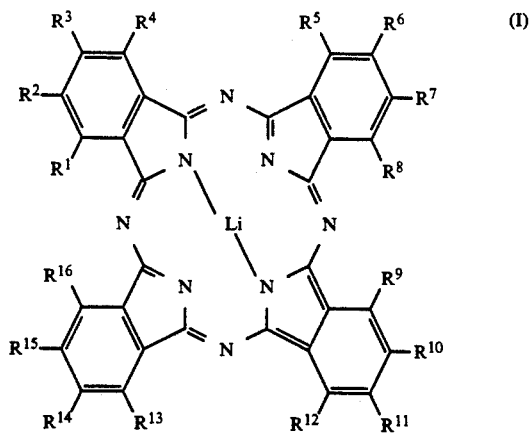

in which $R^2$, $R^3$, $R^6$, $R^7$, $R^{10}$, $R^{11}$, $R^{14}$ and $R^{15}$, which can be the same or different, represent a hydrogen atom, a deuterium atom or an alkyl or alkoxy group with 1–3 carbon atoms, and $R^1$, $R^4$, $R^5$, $R^8$, $R^9$, $R^{12}$, $R^{13}$ and $R^{16}$, which can be the same or different, represent a hydrogen or deuterium atom, provided that all the $R^1$ to $R^{16}$ do not represent a hydrogen atom and examining the EPR signal of the radical lithium phthalocyanine in contact with the said medium.

In this process, the use of a radical lithium phthalocyanine in accordance with formula I makes it possible to obtain a better sensitivity and better accuracy in connection with the measurement of low oxygen levels, particularly due to the presence of the alkyl or alkoxy substituents, or deuterium atoms.

Thus, the peripheral substitution of the phthalocyanine by alkyl or alkoxy groups has the effect of partly sealing the ducts to oxygen. Therefore the oxygen diffusion takes place more between the phthalocyanine layers than in the phthalocyanine columns and consequently there is a faster oxygen response, i.e. a much faster widening of the EPR line of substituted phthalocyanines.

This result could not be forecast on the basis of the performances obtained with known radical lithium phthalocyanine, which had an excessive EPR line width (30,000 nT) and very little line width variation on increasing the oxygen concentration of the medium in which the known radical lithium phthalocyanine is located.

According to a first embodiment of the process according to the invention, the radical lithium phthalocyanine according to the above formula (I) is a lithium phthalocyanine octasubstituted by an alkyl or alkoxy group. The alkyl or alkoxy groups can in particular be the methyl or methoxy group and they are preferably in the $R^2$, $R^3$, $R^6$, $R^7$, $R^{10}$, $R^{11}$, $R^{14}$ and $R^{15}$ positions. The other positions $R^1$, $R^4$, $R^5$, $R^8$, $R^9$, $R^{12}$, $R^{13}$ and $R^{16}$ are occupied by hydrogen atoms.

Octasubstituted lithium phthalocyanines of this type are more particularly described in EP-A-0 352 182 and can be prepared by galvanostatic monoelectronic oxidation of the corresponding octasubstituted dilithium phthalocyanine, as described in EP-A-0 352 182.

According to a second embodiment of the process according to the invention, use is made of an octasubstituted radical lithium phthalocyanine, which is at least partly deuterated.

In this case, the substitution is preferably carried out by a methoxy or methyl group on the $R^2$, $R^3$, $R^6$, $R^7$, $R^{10}$, $R^{11}$, $R^{14}$ and $R^{15}$ positions of formula (I), at least one of the other positions $R^1$, $R^4$, $R^5$, $R^8$, $R^9$, $R^{12}$, $R^{13}$ and $R^{16}$ being occupied by a deuterium atom and the remainder of the latter positions by hydrogen atoms.

Due to the fact that the octasubstituted radical lithium phthalocyanate is deuterated, it is possible to further improve the performance characteristics of said radical substance for the determination of oxygen by EPR spectrometry.

Deuterated, octasubstituted lithium phthalocyanines can also be prepared by the monoelectronic oxidation of the corresponding deuterated, dilithiated precursor. The latter can be obtained by a HD isotopic exchange process between the dilithiated, octasubstituted phthalocyanine and the deuterated tetramethyl pyridine in the presence of a catalyst based on deuterated, lithiated tetramethylpyridine.

According to a third embodiment of the process according to the invention, the radical substance used is an at least partly deuterated radical lithium phthalocyanine. In this case, at least one of the $R^1$ to $R^{16}$ is a deuterium atom and the others represent a hydrogen atom. Preferably, all the $R^1$ to $R^{16}$ are deuterium atoms, because this makes it possible to further improve the EPR characteristics of the radical lithium phthalocyanine and give it a better oxygen sensitivity.

This at least partly deuterated radical lithium phthalocyanine can be prepared by monoelectronic oxidation of the deuterated, dilithiated precursor. The latter can be prepared by H-D isotopic exchange, as in the case of deuterated, octasubstituted radical lithium phthalocyanines.

The radical phthalocyanines of formula (I) used in the process of the invention are very interesting, because the width of their EPR line varies substantially linearly with the oxygen content, in the oxygen concentration range between 0 and 10%.

As a result of these characteristics, it is possible to obtain a better accuracy regarding the measurement of low oxygen levels in biological tissues. Moreover, the high oxygen sensitivity of these phthalocyanines makes it possible either to inject smaller radical substance quantities, if this proves necessary, or to reduce the acquisition time for the EPR curves and in this way obtain a faster response on the metabolisms of organs.

For in vivo oxygen determinations, e.g. in the heart or other organs, it is possible to implant a crystal of the radical phthalocyanine of formula (I) directly in the organ to be examined, or to use a suspension in a liquid of a radical phthalocyanine powder of formula (I), which is injected into the patient to be examined.

The liquids used for preparing such suspensions are non-toxic, biocompatible liquids. For example, it is possible to use $C_4$ to $C_{10}$ alcohols, such as hexanol, $C_4$ to $C_{10}$ polyalcohols, furfuryl alcohols or veratrol.

If necessary, the suspension can also contain other additives, such as agents stabilizing the suspension or regulating its viscosity to an appropriate value.

The radical phthalocyanine concentration of the suspension can vary within a wide range and is preferably in the range 0.1 to 10 mg/l.

Although the radical lithium phthalocyanines used in the process of the invention are not toxic, the doses administered are generally low and can e.g. be 0.01 to 0.1 mg/kg of body-weight.

Following implantation of the crystals or administration of the suspension, it is rapidly possible to carry out the examination by EPR spectrometer.

A method using EPR spectrometry for determining oxygen with the aid of a nitroxide marker such as TANO was described in Journal of Magnetic Resonance, no. 85, pp. 50–59, 1989, but it uses an EPR spectrometer at 9 GHz.

With the phthalocyanine according to the invention, it is possible to carry out measurements not only at 9 GHz, but also at 250 MHz. The use of low frequency is preferable for in vivo or in vitro oximetry in polar solvents such as water.

Thus, the penetration of the magnetic polarization field at 9 to 10 GHz (approximately 3000 Gauss) is only a few millimetres, whereas at 250 MHz penetration and therefore possible measurements can take place over several centimetres (approximately 15 to 20 cm).

If it was necessary to use nitroxides for low frequency oximetry, it would be necessary to increase the quantity used for sensitivity reasons, because the EPR sensitivity drops with the square of the frequency. Thus, to pass from 10 GHz to 250 MHz (ratio of 40) and obtain an equivalent sensitivity, it would be necessary to use $40 \times 40 = 1600$ times more nitroxide and this marker is known to be toxic at doses only a little higher than those used at 9 GHz. However, this is possible with the phthalocyanines according to the invention, because the latter are much more sensitive and consequently the quantities used are lower.

The invention is described in greater detail hereinafter relative to non-limitative embodiments and the attached drawings, wherein show:

FIG. 1 Diagrammatically an apparatus suitable for producing the calibration curve of the radical substance used in the inventive process.

Figure 2:
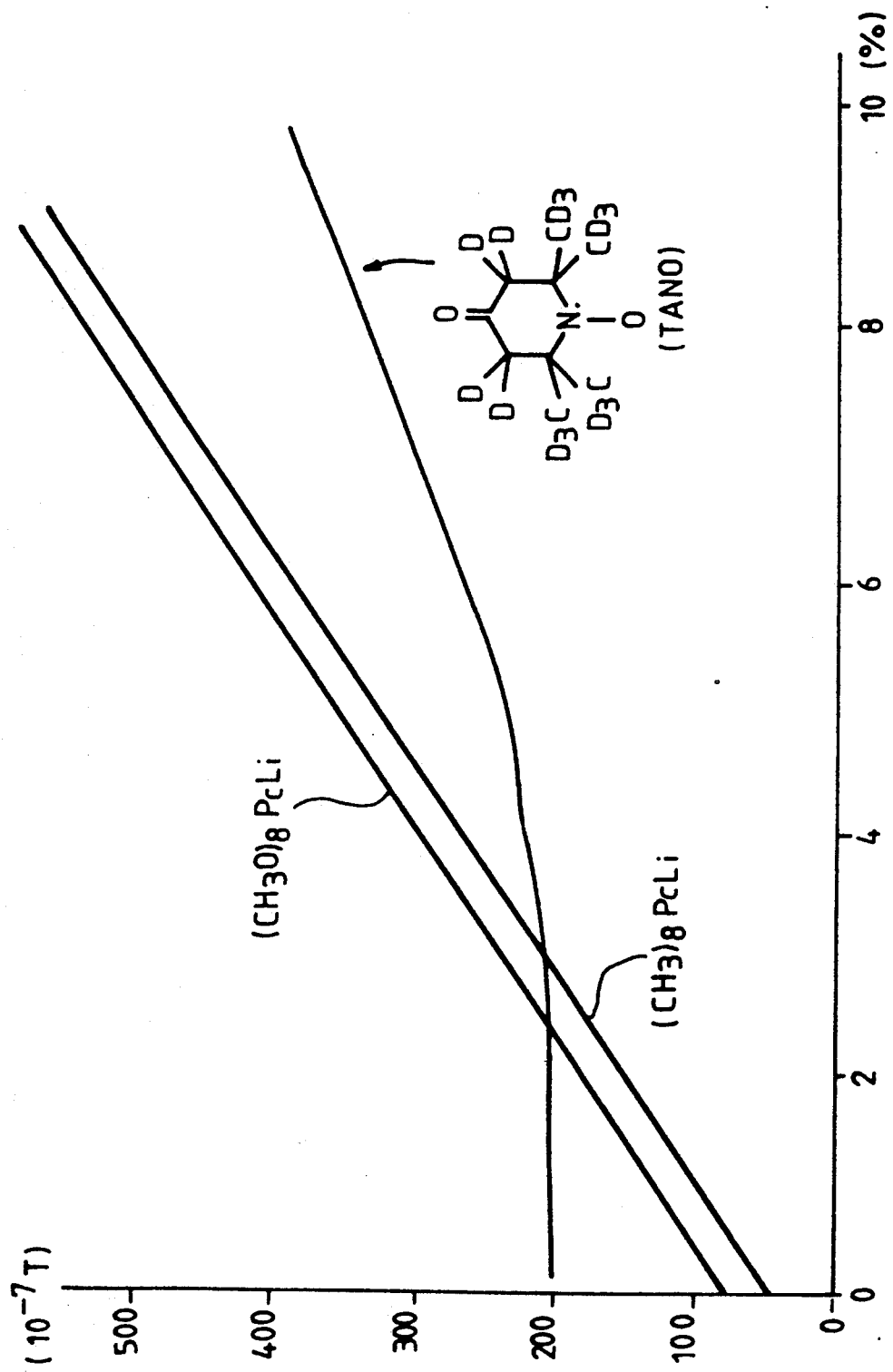

FIG. 2 A graph showing the variations of the EPR line width as a function of the oxygen content of a medium for octasubstituted radical lithium phthalocyanines $(CH_3)_8PcLi$ and $(CH_3O)_8PcLi$ and for a radical substance used in the prior art (TANO).

Figure 3:
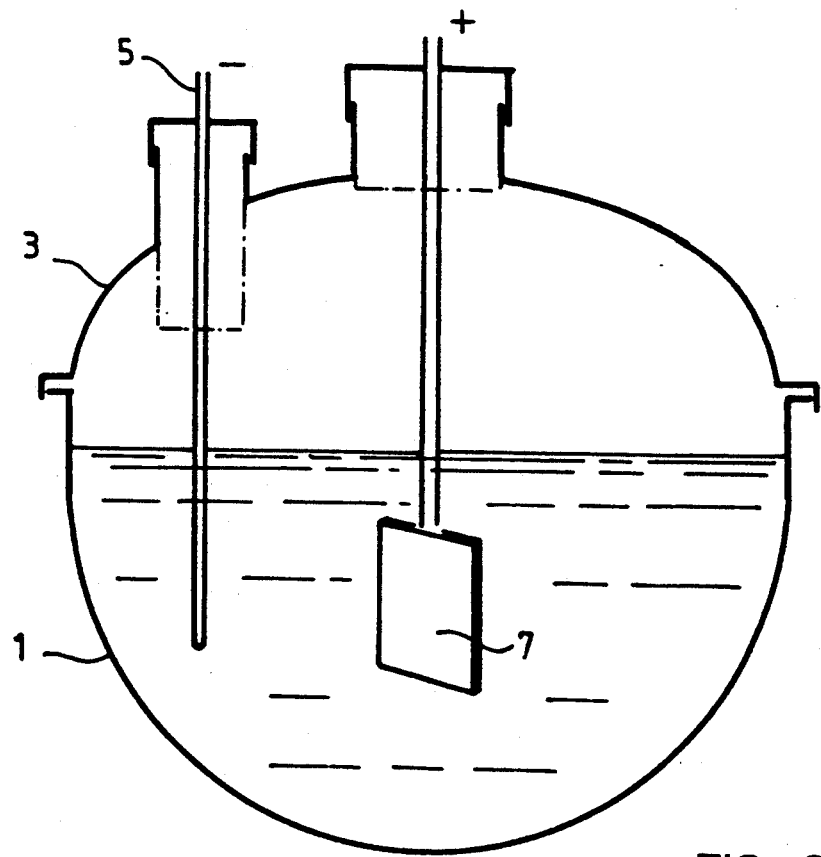

FIG. 3 Diagrammatically shows an electrolytic cell for the preparation of deuterated radical lithium phthalocyanine.

Figure 4:

FIG. 4 A graph showing the EPR signal obtained with deuterated radical lithium phthalocyanine.

Figure 5:
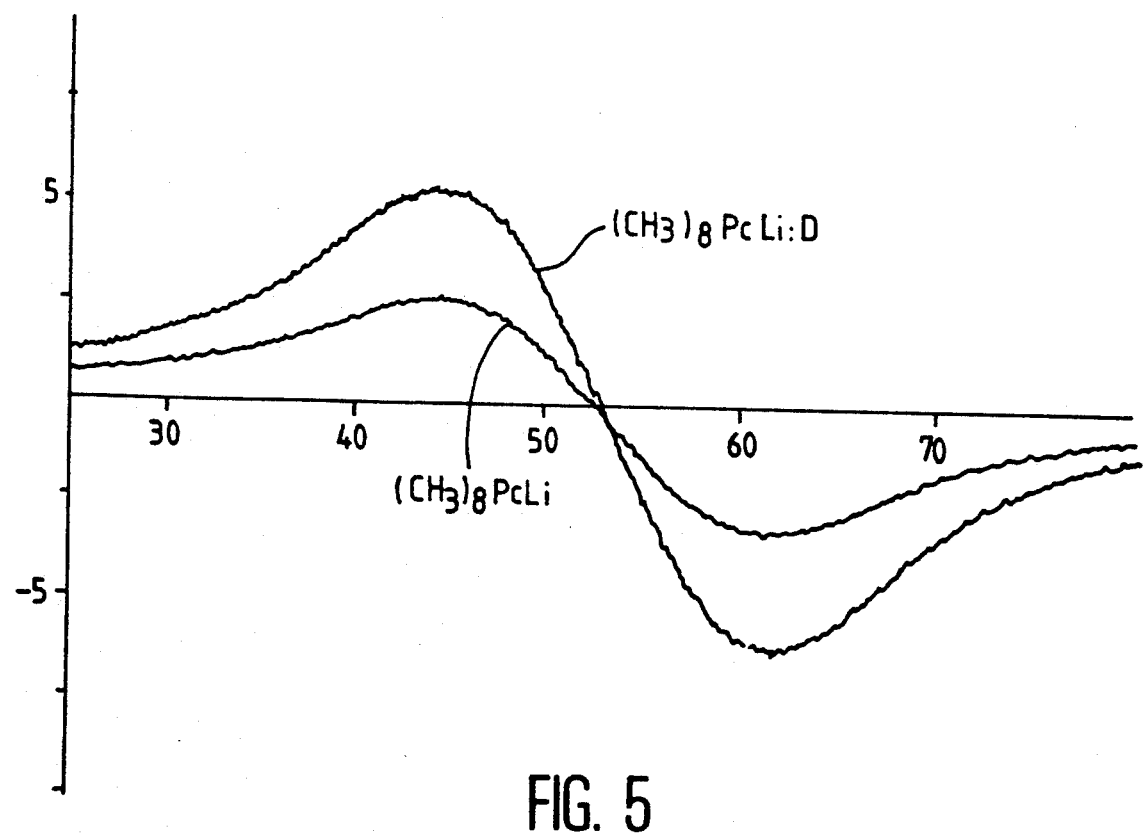

FIG. 5 A graph showing the EPR signal obtained with octasubstituted lithium phthalocyanine $(CH_3)_8(PcLi:H)$ and the partly deuterated, octasubstituted lithium phthalocyanine $(CH_3)_8PcLi:D$.

EXAMPLE 1

This example relates to the use of radical octamethyl lithium phthalocyanine for measuring oxygen concentrations from 0 to 10%.

The radical octamethyl lithium phthalocyanine is prepared from octamethyl dilithium phthalocyanine using the same operating procedure as in example 2 of EP-A- 0 352 182.

This is followed by the determination of the EPR characteristics of radical octamethyl lithium phthalocyanine in the characteristics of radical octamethyl lithium phthalocyanine in the presence of different oxygen concentrations in order to obtain the calibration curve corresponding to the variations of the EPR line width as a function of the oxygen content of the medium.

For this purpose, into a tube are introduced the previously obtained octasubstituted, radical lithium phthalocyanine crystals and then a vacuum is formed in the tube. The width of the EPR line is then measured after introducing the tube, kept under a vacuum, into an EPR spectrometer. The same measurements are then repeated after contacting the crystals with different oxygen quantities.

This can be carried out by using the apparatus diagrammatically shown in FIG. 1. This apparatus has a vacuum system 11 provided with a pumping group 13 for forming a vacuum in the system, which can be connected via a valve 15 to a tube 17 containing the lithium phthalocyanine crystals and by a valve 19 to a container 21 containing a given oxygen volume.

To carry out the first measurement, the valve 15 is opened after placing the tube 17 on the apparatus and forming the vacuum with the pumping group 13. The valve 15 is then closed again and the sealed tube 17 is introduced into the EPR spectrometer. Following this measurement, the tube 17 is again placed on the vacuum system 11. The valves 15 and 19 are then opened to contact the lithium phthalocyanine with the given oxygen volume of the container 21. Following said contacting, the valve 15 is closed and the tube 17 introduced into the EPR spectrometer in order to obtain the line width at 9 GHz.

After this operation, the lithium phthalocyanine is degassed by placing the tube 17 on the vacuum system 11 and forming a vacuum in the installation. The degassed phthalocyanine is then contacted with another oxygen volume using another container 21. This gives the values of the EPR line width of said phthalocyanine as a function of the oxygen concentration.

FIG. 2 gives the EPR line width variation curve (in $10^{-7}$T) of $(CH_3)_8$PcLi, as a function of the oxygen content in percent. It is possible to see that the variation of the line width is linear in the concentration range from 0 to 10% and that it is possible to detect very small oxygen content variations in this concentration range.

FIG. 2 shows for comparison purposes the variations of the EPR line width obtained under the same conditions with TANO, which was previously used for oxygen determination by EPR.

On comparing these two curves, it can be seen that TANO does not make it possible to detect oxygen concentration variations in the range 0 to 6%, which clearly demonstrates the interest of the invention.

EXAMPLE 2

This example uses the same operating procedure as in example 1 for determining the variations of the EPR line width of radical octamethoxy lithium phthalocyanine prepared following the operating procedure of example 1 of EP-A-0 352 182. The results obtained are given in FIG. 2 for this lithium phthalocyanine $(CH_3O)_8$PcLi.

It can be seen that the variation of the EPR line width of $(CH_3O)_8$PcLi is also linear in the concentration range from 0 to 10% and that the sensitivity is better than that of $(CH_3)_8$PcLi.

Thus, this octasubstituted, radical lithium phthalocyanine also has much better performance characteristics than TANO, because it makes it possible to detect low oxygen variations in the concentration range from 0 to 10%.

EXAMPLE 3

Preparation of lithium deuterated phthalocyanine.

In this example, deuterated, radical lithium phthalocyanine is prepared from its deuterated, dilithiated precursor.

a) Preparation of deuterated, dilithiated phthalocyanine

For this preparation, dilithiated lithium phthalocyanine is contacted with ($^2$H)-2,2,6,6-tetramethylpiperidine. The latter was prepared by H-D isotopic exchange between commercially available tetramethylpyridine (TMP) and $^2H_2O$ at ambient temperature, followed by a separation of the organic phase and the aqueous phase by ether addition.

The exchange between the dilithiated phthalocyanine and the deuterated TMP was carried out in the presence of lithium tetramethylpiperidine, which serves as the catalyst, by mixing all the reagents in tetrahydrofuran at $-23°$ C.

Under these conditions, the isotopic exchange takes place selectively on the positions corresponding to $R^1$, $R^4$, $R^5$, $R^8$, $R^9$, $R^{12}$, $R^{13}$ and $R^{16}$ of formula (I). Thus, the exchange is repeated several times to obtain the entirely deuterated lithium phthalocyanine of formula (I), i.e. in which $R^1$ to $R^{16}$ are deuterium atoms.

The deuterium exchange is followed by nuclear magnetic resonance of the proton, because the replacement of the hydrogen atoms by deuterium in the positions corresponding to $R^1$, $R^4$, $R^5$, $R^8$, $R^9$, $R^{12}$, $R^{13}$ and $R^{16}$ leads to the appearance of singlets on the nuclear magnetic resonance spectrum of the proton, whereas in the case when there are two hydrogen atoms in the adjacent positions $R^1$-$R^2$ or $R^3$-$R^4$, etc., the coupling between the protons gives a NMR signal constituted by two multiplets (quadruplets) at 8 and 9.2 ppm.

b) Preparation of deuterated, radical lithium phthalocyanine.

The electrolytic cell shown in FIG. 3 is used for this preparation. FIG. 3 shows very diagrammatically an electrolytic cell usable for preparing deuterated, radical lithium phthalocyanine powder according to the invention. The cell 1 is hemispherical and is tightly sealed by a cover 3. Within the cell are placed a cathode 5 constituted by a platinum metal wire, e.g. having a diameter of 1 mm and a length of 4 cm, as well as an anode 7 constituted by a 25×35 mm platinum plate. The anode and the cathode are connected to a current generator equipped with an appropriate device making it possible for the cell to operate according to the intensiostatic or galvanostatic method.

Into the cell 1 are introduced 300 mg of deuterated, dilithiated phthalocyanine previously obtained in solution in 500 ml of ultra-anhydrous acetonitrile. The acetonitrile used has a water content below 50 ppm and, just prior to use, it is passed on to a column of basic alumina powder of activity I having a diameter of 5 cm and a height of 10 cm, in order to eliminate any acetic acid traces therein. Into the cell are also introduced 400 mg of a support electrolyte constituted by tetrabutyl ammonium hexafluorophosphate, which was recrystallized 5 times in ethanol and dried in vacuo for 24 h at 80° C.

After sealing the electrolytic cell, electrosynthesis is carried out using a constant current of 5 μA for 24 h, then a constant current of 20 μA for 48 h and then a constant current of 50 μA for 72 h.

At the end of the operation, 150 mg of deuterated, radical lithium phthalocyanine are collected. The latter was substantially the same performance characteristics as $(CH_3)_8PcLi$ for oxygen determination.

FIG. 4 shows the EPR signal obtained at 9 GHz with the partly deuterated lithium phthalocyanine (PcLi:D) previously prepared. It is also possible to see in dotted line form the signal obtained under the same conditions with the prior art lithium phthalocyanine prepared by potentiostatic monoelectronic oxidation at +0.5 V of the dilithiated precursor and as described by Sugimoto et al in J. Chem. Soc. Chem. Commun., 1986, pp. 962/3.

FIG. 4 shows that the signal obtained with the partly deuterated lithium phthalocyanine has a much more pronounced slope and therefore a better sensitivity than that obtained with undeuterated lithium phthalocyanine. Thus, the finer the signal obtained, the more readily the low EPR line width variations are detectable and the lower the detected oxygen quantities.

EXAMPLE 4

As in example 2 of EP-A-0 352 182, deuterated octamethyl lithium phthalocyanine was prepared starting from its deuterated, dilithiated precursor prepared in the same way as in example 3 above.

This is followed by the examination in an EPR spectrometer the lithium phthalocyanine octasubstituted by methyl groups and partly deuterated on the positions corresponding to $R^1, R^4, R^5, R^8, R^9, R^{12}, R^{13}$ and $R^{16}$ of formula (I).

The results obtained are given in FIG. 5, which shows the EPR signal of said phthalocyanine $(CH_3)_8PcLi:D$. FIG. 5 also shows the EPR signal of the undeuterated, substituted octamethyl phthalo cynanine $(CH_3)_8PcLi$ obtained under the same conditions.

It is clear that the substitution by deuterium makes it possible to obtain better EPR characteristics, because the slope of the signal is more marked in the case of $(CH_3)_8PcLi:D$.

I claim:

1. A process for the detection or determination of molecular oxygen in a medium, comprising contacting said medium with a radical lithium phthalocyanine according to formula (I):

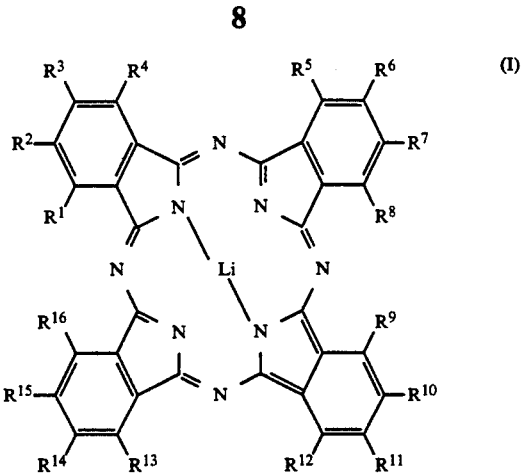

2. The process according to claim 1, wherein $R^2, R^3, R^6, R^7, R^{10}, R^{11}, R^{14}$ and $R^{15}$ represent methyl groups and $R^1, R^4, R^5, R^8, R^9, R^{12}, R^{13}$ and $R^{16}$ represent hydrogen.

3. The process according to claim 1, wherein $R^2, R^3, R^6, R^7, R^{10}, R^{11}, R^{14}$ and $R^{15}$ represent methoxy groups and $R^1, R^4, R^5, R^8, R^9, R^{12}, R^{13}$ and $R^{16}$ represent hydrogen.

4. The process according to claim 1, wherein the alkyl groups are methyl groups and the alkoxy groups are methoxy groups and at least one of the $R^1, R^4, R^5, R^8, R^9, R^{12}, R^{13}$ and $R^{16}$ represent a deuterium with the remainder being hydrogen.

5. The process according to claim 1, wherein at least one of $R^1, R^4, R^5, R^8, R^9, R^{12}, R^{13}$ and $R^{16}$ represent a deuterium.

6. A composition usable for detection or determination of molecular oxygen comprising: a suspension of radical lithium phthalocyanine powder of formula (I):

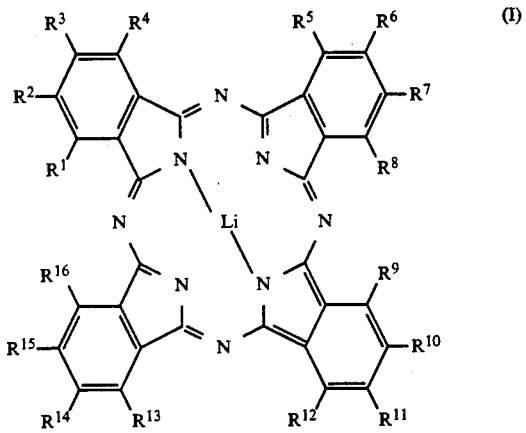

in which $R^2, R^3, R^6, R^7, R^{10}, R^{11}, R^{14}$ and $R^{15}$, which can be the same or different are selected from the group consisting of alkyl and alkoxy groups with 1 to 3 carbon atoms and the $R^1, R^4, R^5, R^8, R^9, R^{12}, R^{13}, R^{16}$, which can be the same or different, are selected from the group consisting of hydrogen and deuterium.

in a non-toxic biocompatible liquid selected from the group consisting of $C_4$ to $C_{10}$ alcohols, furfuryl alcohol, $C_4$ to $C_{10}$ polyols, and veratrol.

7. The composition according to claim 6, wherein the $R^2, R^3, R^6, R^7, R^{10}, R^{11}, R^{14}$ and $R^{15}$ represent methyl groups and $R^1, R^4, R^5, R^8, R^9, R^{12}, R^{13}$ and $R^{16}$ represent hydrogen.

8. The composition according to claim 6, wherein the $R^2$, $R^3$, $R^6$, $R^7$, $R^{10}$, $R^{11}$, $R^{14}$ and $R^{15}$ represent methoxy groups and the $R^1$, $R^4$, $R^5$, $R^8$, $R^9$, $R^{12}$, $R^{13}$ and $R^{16}$ represent hydrogen.

9. The composition according to claim 7, wherein the alkyl groups are methyl groups and the alkoxy groups are methoxy groups and at least one of the $R^1$, $R^4$, $R^5$, $R^8$, $R^9$, $R^{12}$, $R^{13}$, and $R^{16}$ represent deuterium, with the remainder being hydrogen.

10. The composition according to claim 6, wherein at least one of $R^1$, $R^4$, $R^5$, $R^8$, $R^9$, $R^{12}$, $R^{13}$, and $R^{16}$ represent a deuterium.

* * * * *